United States Patent
Nakagawa

[11] Patent Number: 6,164,964
[45] Date of Patent: *Dec. 26, 2000

[54] ORTHODONTIC APPLIANCE AND BRACKET

[75] Inventor: Katsuyuki Nakagawa, Otawara, Japan

[73] Assignee: Sankin Kogyo Kabushiki Kaisha, Otawara, Japan

[*] Notice: This patent is subject to a terminal disclaimer.

[21] Appl. No.: 09/335,907

[22] Filed: Jun. 18, 1999

Related U.S. Application Data

[62] Division of application No. 08/963,856, Nov. 4, 1997, Pat. No. 6,095,808.

[30] Foreign Application Priority Data

Jun. 13, 1997 [JP] Japan .................................. 9-157004

[51] Int. Cl.$^7$ .................................................. A61C 3/00
[52] U.S. Cl. .................................................. 433/9; 433/10
[58] Field of Search ........................... 433/8, 9, 10, 13, 433/15, 16

[56] References Cited

U.S. PATENT DOCUMENTS

| | | |
|---|---|---|
| 3,469,314 | 9/1969 | Pearlman . |
| 3,930,311 | 1/1976 | Andrews . |
| 4,193,195 | 3/1980 | Merkel et al. . |
| 4,249,897 | 2/1981 | Anderson . |
| 4,299,569 | 11/1981 | Frantz . |
| 4,302,532 | 11/1981 | Wallshein . |
| 5,125,831 | 6/1992 | Pospisil . |
| 5,254,002 | 10/1993 | Reher et al. . |
| 5,358,402 | 10/1994 | Reed et al. . |
| 5,380,196 | 1/1995 | Kelly et al. . |
| 5,595,484 | 1/1997 | Orikasa et al. . |
| 5,597,302 | 1/1997 | Pospisil et al. . |
| 5,618,175 | 4/1997 | Reher et al. . |

FOREIGN PATENT DOCUMENTS 196 06 423  9/1996  Germany .

OTHER PUBLICATIONS

Sankin Kogyo Kabushiki Kaisha, Apr. 1996, "Clear Bracket, Orthodontic Composite Bracket" (With Partial English Translation).

*Primary Examiner*—Ralph A. Lewis
*Attorney, Agent, or Firm*—Oblon, Spivak, McClelland, Maier & Neustadt, P.C.

[57] ABSTRACT

An orthodontic appliance of the present invention has a combination of a bracket with a hook and a bracket without a hook.

The bracket with a hook includes a metal body formed with a groove therein adapted for being engaged with an arch wire and provided with a hook thereon, the hook is integrally formed with the metal body; and a synthetic resin housing for accommodating the metal body therein such that inner surface of the groove is exposed and at least top portion of the hook projects from the synthetic resin housing. The bracket without a hook includes a metal body formed with a groove therein adapted for being engaged with an arch wire; and a synthetic resin housing for accommodating the metal body therein such that inner surface of the groove is exposed.

13 Claims, 16 Drawing Sheets

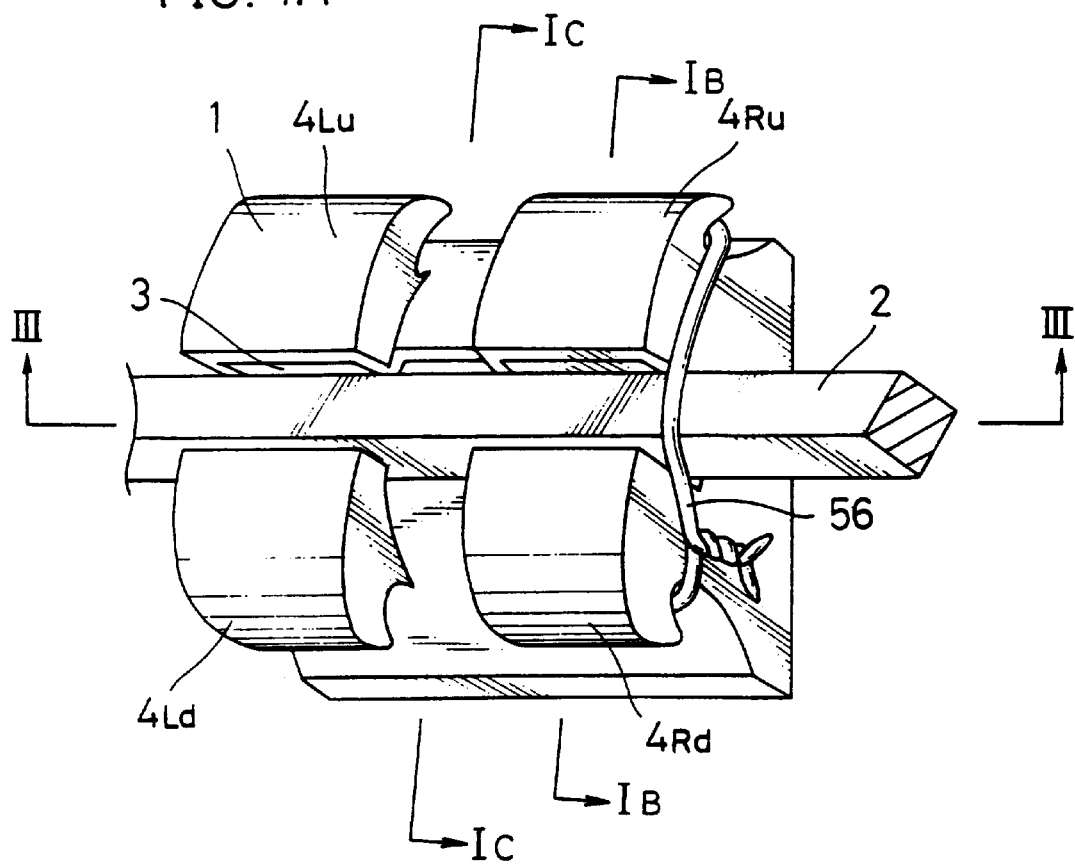
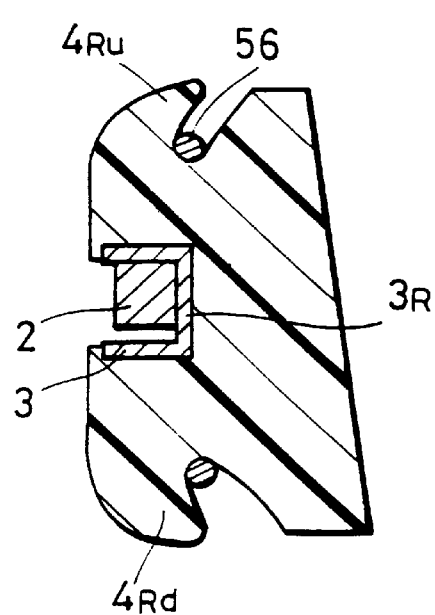
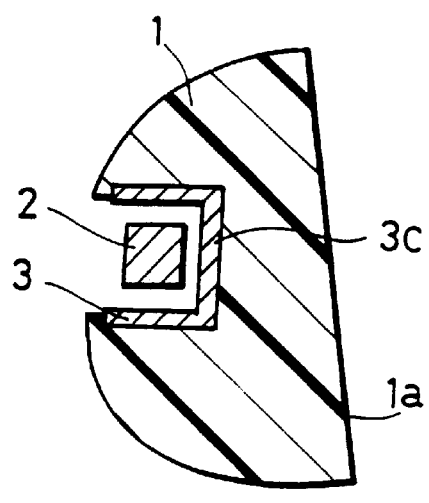

FIG. 10A
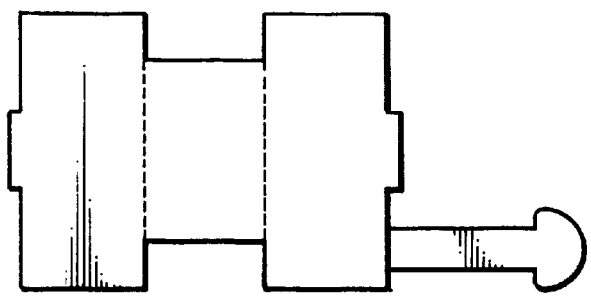
FIG. 10B
FIG. 10C-1          FIG. 10C-2
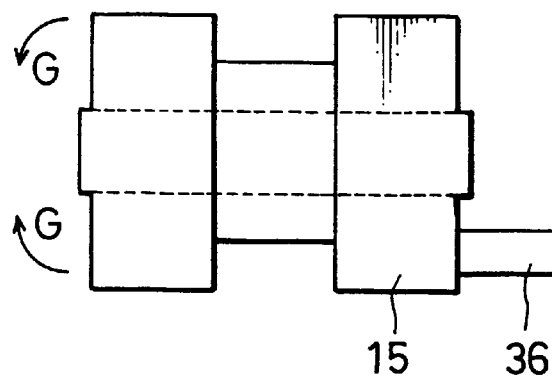 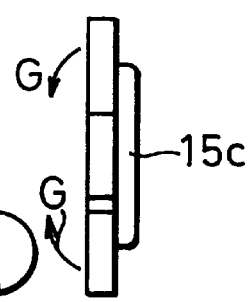
FIG. 10D            FIG. 10E
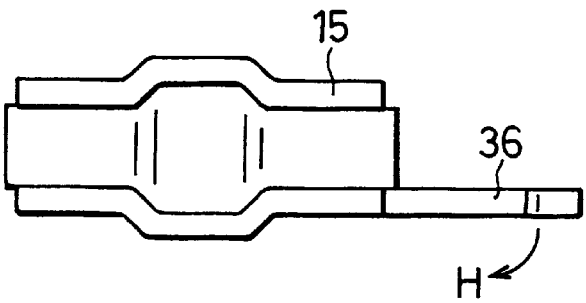 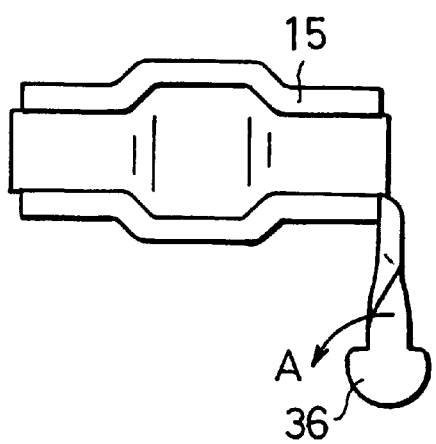

6,164,964

ORTHODONTIC APPLIANCE AND BRACKET

This application is a division of Ser. No. 08/963,856, filed Nov. 4, 1997, now U.S. Pat. No. 6,095,808.

BACKGROUND OF THE INVENTION

1. Field of the Invention

The present invention relates to a bracket and an orthodontic appliance for use in an orthodontic treatment.

2. Description of the Related Art

An irregular row of teeth detracts from ones appearance. In addition, plaque is likely to accumulate on teeth in an irregular row, causing dental caries and pyorrhoea alveolaris. In order to prevent such problems, orthodontic treatments have been widely conducted.

Commonly, an orthodontic treatment is conducted by the following steps. First, a bracket is attached onto the surface of tooth to be treated by an adhesive and the like. The bracket is formed with a groove to be engaged with an arch wire. In this state, the arch wire applies a pushing force, a pulling force or a twisting force onto the tooth via the bracket (hereinafter, such forces are referred to as an orthodontic force). Due to the application of the orthodontic force, the tooth is moved to a desired position in a desired direction. The bracket may also have a hook. When two or more teeth are respectively provided with a bracket with a hook, the brackets are connected to each other by putting a rubber ring or a spring around the hooks, and at the same time an arch wire is engaged to the grooves of the brackets. In this state, an orthodontic force is applied to the tooth to be treated by the arch wire and the rubber ring, thereby moving the tooth to the desired position in a desired direction.

Conventionally, a bracket is mainly made of metal (Conventional Example 1). The metal bracket is shiny and is conspicuous, and therefore, the orthodontic treatment using such brackets may be considered unaesthetic. To avoid such a problem, in recent years a bracket made of a synthetic resin or ceramics has been suggested (Conventional Example 2). As the synthetic resin bracket and the ceramics bracket are a milk white color, transparent, or semi-transparent, the appearance of the bracket is inconspicuous when attached to a tooth.

However, the synthetic resin bracket and ceramics bracket have many physical disadvantages as compared with the metallic bracket. For example, when an arch wire is engaged to the groove of the bracket, large friction is generated between the arch wire and the groove of the housing. Due to the large friction, the arch wire cannot smoothly slide in the groove, and the inner surface of groove in contact with the arch wire may be worn out or cracked. As a result, an orthodontic force is not properly applied to the tooth to be treated.

To reinforce the portion of the groove brought into contact with the arch wire, a bracket including a housing made of synthetic resin or ceramics and a metal body accommodated thereto has been suggested (Conventional Example 3). The metal body is formed with a groove therein adapted for being engaged with an arch wire. As described above, the inner surface of the groove brought into contact with the arch wire is likely to be worn out. If the inner surface of the groove is worn out, a proper force application is impossible, so that the tooth to be treated cannot be moved in a desired direction. In contrast, in Conventional Example 3, the bracket includes a metal body in the housing. The metal body is excellent in abrasion resistance, and an arch wire can smoothly slide in the metal body. Accordingly, a proper orthodontic force can be continuously applied to the tooth for a long period of time.

FIG. 13 is a perspective view showing a bracket 52 without a hook according to Conventional Example 3. FIG. 14A is a perspective view showing a state in which an arch wire 2 is engaged to a groove of the bracket 52. FIG. 14B is a cross-sectional view showing the bracket 52, taken along the line $XIV_B$—$XIV_B$ in FIG. 14A.

As described above, the bracket 52 includes a housing made of synthetic resin and formed with a groove therein, and a metal body formed with a groove and accommodated to the housing. In FIGS. 13, 14A, and 14B, the bracket of Conventional Example 3 is a twin-type bracket having two pairs of wings $51_{Ru}$, $51_{Rd}$ and $51_{Lu}$, $51_{Ld}$.

In the orthodontic treatment, the housing 52 is attached to the tooth to be treated (not shown) by its adhesion side 52a, and the arch wire 2 is engaged to the groove 50. In this state, as shown in FIG. 14A, a fastening wire 56 such as metal wire is put around the pair of wings $51_{Ru}$, $51_{Rd}$ to tightly fix the arch wire 2 to the bracket 52. Or alternatively, the fastening wire may be put around both the pairs of wings $51_{Ru}$, $51_{Rd}$ and $51_{Lu}$, $51_{Ld}$. In addition, the fastening wire 56 is not limited to a metal wire, but may be other parts such as a rubber ring.

FIG. 15 is a perspective view showing a bracket 62 with a hook according to Conventional Example 3. The bracket 62 is a single-type bracket formed with a pair of wings 61, 61 as a one-piece unit. The bracket 64 includes a housing made of synthetic resin formed with a groove, and a metal body 65 accommodated thereto.

In an orthodontic treatment, a bracket 62 is attached to the surface of a tooth to be treated (not shown), and an arch wire is engaged to the groove of the metal body 65. In this state, a fastening wire is put around the wings 61, 61 so as to firmly fix the arch wire to the bracket 62. At the same time, the bracket 62 is connected to another bracket 62 attached to another tooth by putting a rubber ring around their hooks, so that these teeth may be moved toward each other.

There are various shapes of brackets. Examples thereof include: a twin-type bracket formed with two pairs of wings without hook, such as shown in FIGS. 13 and 14; a single-type bracket formed with a pair of wings without hook; a single-type bracket formed with a pair of wings, one of which has a hook on its end, such as shown in FIG. 15; and a twin-type bracket formed with two pairs of wings one of which has a hook on its end. These may be used in combination in an orthodontic treatment.

An orthodontic treatment is conducted by the following steps. In the first step, an irregular row of teeth is roughly corrected (hereinafter, this step is referred to as a rough treatment step). At this stage, the arch wire need not to be firmly fixed to the bracket, and there is some clearance between the arch wire and the groove of the bracket. Without the clearance, an excessive force is applied to the tooth. The excessive force to the tooth not only causes inconvenience to the patient, but also moves the tooth to an extent beyond that necessary. As a result, the local treatment is excessive, and the row of teeth cannot be adjusted in a desirable manner.

In order to avoid the above-described disadvantage, in a rough treatment step, an arch wire having a round cross-section is generally used, and the arch wire is loosely fixed to the bracket. More specifically, the arch wire has a round cross-section and the groove is in a form of U-shaped square enclosed with flat side surfaces and a flat bottom surface. With this structure, when engaged to the groove, the arch wire is brought into point contact with the groove. In addition, the arch wire having a round cross-section easily changes its contact point with the groove when being twisted and the like. Furthermore, in the rough treatment step, a fastening wire is loosely put around the wings of the bracket. Therefore the arch wire and the bracket are loosely fixed to each other. In this state, the row of teeth is roughly adjusted to a desired alignment.

When the rough adjustment of the row of teeth is completed, the row of teeth is precisely adjusted (hereinafter, this step is referred to as a precise treatment step). As shown in FIG. 14A, an arch wire 2 used in the precise treatment step has a square cross-section. The arch wire 2 is engaged to the groove 50 of the bracket 52, and in this state, the fastening wire 56 is strongly put around the wings $51_{Ru}$, $51_{Rd}$ so as to tightly fix the arch wire 2 to the bracket 52. As the arch wire 2 having a square shape is strongly pushed toward the bottom of the groove 50, the arch wire 2 does not roll inside the groove. In this state, a torque is continuously applied to a tooth to be treated at a desired torque angle θ, whereby the tooth is moved to a desired position in a desired direction.

In general, a single-type bracket is advantageous for its small size. However, the single-type bracket is attached to the tooth in such a manner that the center of its wing along a direction perpendicular to the groove is positioned to the center of the tooth along the direction perpendicular to the groove. Therefore, there is a disadvantage that the right and left portions of one tooth cannot be treated by an independent force. Contrary to this, a twin-type bracket has an advantage that, when an arch wire is fixed to the bracket, the two pairs of wings of the bracket are used individually or in combination, depending on the necessity. In this manner, the tooth can be easily controlled to move in various directions. The use of the twin-type bracket is especially desirable in a precise treatment step.

However, as compared with the twin-type bracket made of metal, the twin-type bracket including a synthetic resin housing and a metal body, such as that of Conventional Example 3, has disadvantages as follows.

FIG. 16 is a cross-sectional view showing a bracket 52 of FIG. 14A taken along the line XVI—XVI. The identical components to FIG. 14A are designated by the same reference numerals, and the description thereof will be omitted.

The bracket 52 includes a metal body 53 produced by bending a flat metal plate into a U-shape. Therefore, the metal body 53 is enclosed with flat surfaces. When an arch wire 2 is engaged to the groove 50 fitted with the metal body 53 and then a fastening wire 56 is put around the wings $51_{Ru}$, and $51_{Lu}$, the arch wire 2 is firmly fixed to bracket 52 only at the one end portion β. Therefore, the fastening wire 56 cannot firmly fix the arch wire 2 to the bracket 52 at the middle portion of the metal body 53. For firm fixation, it is necessary to put the fastening wire 56 around both pairs of wings. When the fastening wire is put around both pairs of wings, the control of the row of teeth is difficult and insufficient.

If the firm fixation of the arch wire 2 to the bracket 52 is successfully conducted by putting the fastening wire 56 around only one pair of wings, a uniform force is applied to the bracket over the entire length of the groove of the metal body 53. That is, the force is equivalent to that of the case of putting a fastening wire around two pairs of wings. As a result, it is impossible to treat the right and left portions of the tooth by an independent force. Practically, the conventional twin-type bracket only has a function of the single-type bracket.

As an attempt to solve the above-described problem, it has been suggested that a metal body is provided to the groove of housing only at the portions corresponding to the wings, and the middle portions of the groove of the housing is not provided with a metal body. With this structure, however, the bracket has poor strength and therefore is easily bent.

When a bracket is entirely made of metal, it may be advantageously used as a twin-type bracket. The twin-type bracket made of metal can be used in many applications. In contrast, as has already described above, the bracket of Conventional Example 3 including a synthetic resin housing and a metal body accommodated thereto has several problems.

In addition, the brackets 52, 62 of Conventional Example 3 have a further problem. That is, by being enclosed with the flat surfaces, the metal bodies 53, 65 cannot resist a force applied to their side surfaces in the width direction. Therefore, the metal body may be easily deformed.

Moreover, the bracket of Conventional Example 3 having a hook has further problems as follows. As described above, the bracket made of synthetic resin or ceramics has a strength smaller than the bracket made of metal. Therefore, the bracket made of synthetic resin and ceramics is required to have a hook larger in size than that of the bracket made of metal (see FIG. 15). However, when such a bracket is attached to the tooth, a large hook is brought into contact with the gingiva, bucca, and lips, which gives a sense of discomfort to the patient. In addition, plaque tends to accumulate on the large hook, which makes the inside of the mouth insanitary.

The hook made of synthetic resin or ceramics cannot be bent. Therefore, even if the hook is brought into contact with the gingiva, it cannot be apart from the gingiva. This may cause inflammation of the gingiva.

Contrary to this, when the bracket with a hook is entirely made of metal (Conventional Example 1), the hook can be small in size while having a sufficient strength. In addition, the hook can be bent. Accordingly, in a practical treatment, a metal bracket with a hook is widely used. However, the appearance of the bracket as a whole is deteriorated when a metal bracket is used.

SUMMARY OF THE INVENTION

It is an object of the present invention to solve the above-described problems, and to provide an orthodontic appliance and bracket for use in an orthodontic treatment.

According to one form of the invention, an orthodontic appliance comprises a bracket with a hook including a metal body formed with a groove therein adapted to be engaged with an arch wire and provided with a hook integrally formed thereon. A synthetic resin housing accommodates the metal body therein such that inner surface of the groove is exposed and at least top portion of the hook projects from the synthetic resin housing. A bracket without a hook includes a metal body is formed with a groove therein and is adapted to be engaged with an arch wire. A synthetic resin housing accommodates the metal body therein such that the inner surface of the groove is exposed. The hook has an elongated element which is elongated in a direction different than a direction of the length of the groove, preferably in a direction substantially perpendicular to a direction of the length of the groove.

According to another form of the invention, a bracket with a hook comprises a metal body formed with a groove therein adapted for being engaged with an arch wire and provided with a hook integrally formed thereon. A synthetic resin housing accommodates the metal body therein such that inner surface of the groove is exposed and at least top portion of the hook projects from the synthetic resin housing.

According to yet another form of the invention, a single-type bracket includes a synthetic resin housing and a metal body, and the metal body is configured such that the space of the groove formed therein is enlarged in the middle of the bracket.

These and other objects, features and advantages of the present invention will become more apparent upon reading the following detailed description along with accompanying drawings.

BRIEF DESCRIPTION OF THE DRAWINGS

FIGS. 10A to 10E are diagrams illustrating the steps of manufacturing a metal body for the groove and a hook of the bracket of Example 5;

DESCRIPTION OF THE PREFERRED EMBODIMENTS

Figure 2A:
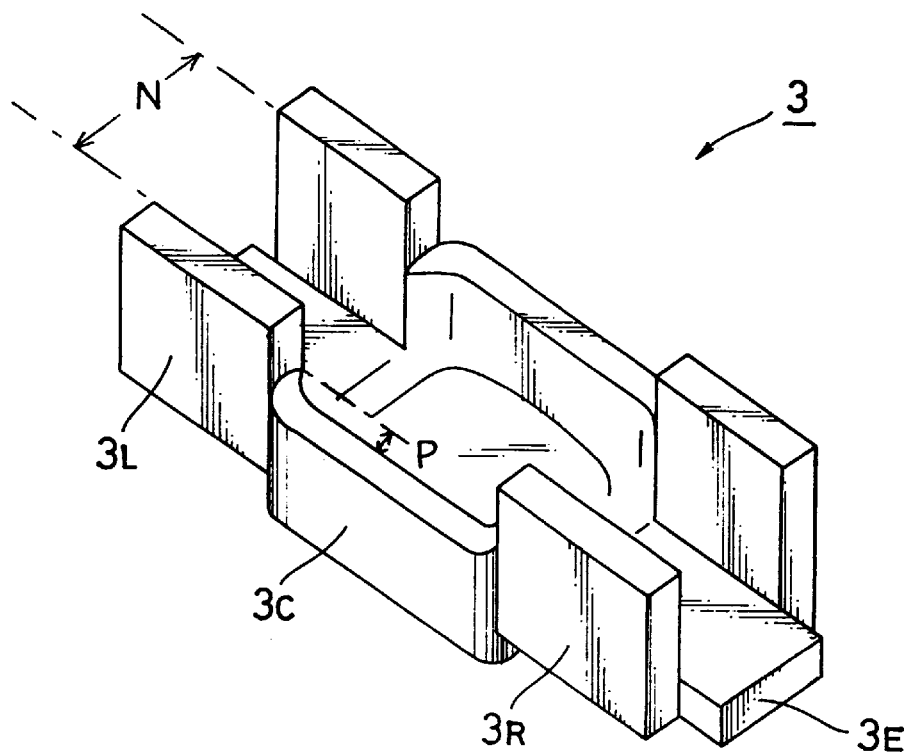
FIG. 2A is a perspective view showing a metal body of the bracket of Example 1.

Hereinafter, the first invention will be described. According to the first invention, an orthodontic appliance comprises a bracket with a hook and a bracket without a hook. The bracket with a hook includes a metal body formed with a groove therein adapted for being engaged with an arch wire and provided with a hook integrally formed thereon. A synthetic resin housing accommodates the metal body therein such that inner surface of the groove is exposed and at least top portion of the hook projects form the synthetic resin housing. The bracket without a hook includes a metal body formed with a groove therein adapted for being engaged with an arch wire and a synthetic resin housing for accommodating the metal body therein such that inner surface of the groove is exposed. The hook has an elongated element which is elongated in a direction different than a direction of the length of the groove, preferably in a direction substantially perpendicular to a direction of the length of the groove.

In the first invention, preferably, the metal body of the bracket is configured such that a space of the groove formed therein is enlarged in the middle of the bracket in its plan view. The metal body of the bracket is configured such that a depth and a width of the groove formed therein are enlarged in the middle of the bracket in its plan view.

As the metal body is formed with a groove having an enlarged portion, the bracket is resistive against abrasion and bending forces, and an arch wire can be firmly engaged. When a twin-type bracket has such a structure, high performance can be attained in treatment, and the tooth to be treated can be easily controlled to move in any desirable directions. In addition, as the bracket has a synthetic resin housing, the appearance of the bracket as a whole is not deteriorated.

Next, the second invention will be described. In the second invention, a bracket with a hook includes a metal body formed with a groove therein adapted for being engaged with an arch wire and provided with a hook integrally formed thereon. A synthetic resin housing accommodates the metal body therein such that inner surface of the groove is exposed and at least top portion of the hook projects from the synthetic resin housing.

The hook made of metal has a sufficient strength while being small in size, and can be easily bent. However, if the metal hook is simply attached to the housing made of synthetic resin or ceramics, the force applied to the hook during the treatment easily detaches the hook from the housing. Therefore, the hook is integrally formed with the metal body. The metal body and the metal hook are formed as one-piece unit. They may be manufactured as one-piece unit, or may be manufactured as separate pieces, and then welded together to form one-piece unit. With a one-piece structure, the hook is never detached from the metal body even in the application of force during the treatment. Accordingly, a force required for the treatment can be properly transferred to the tooth. Or alternatively, the hook and the metal body may be formed in one-piece unit by casting or powder injection molding. Also in this case, the hook is firmly attached to the metal body, whereby a force required for the treatment can be properly transferred to the tooth.

As described above, the metal hook has a sufficient strength while being small in size, and can be bent. Also, the synthetic resin housing may be milk white or transparent, so that the appearance of the bracket as a whole is not deteriorated.

According to the second invention, the bracket with a hook has advantages as follows: 1) as the synthetic resin housing may be milk while or transparent, the appearance of the bracket as a whole is not deteriorated when the bracket is attached to the tooth; 2) as the hook is firmly attached to the metal body, the hook is never detached from the synthetic resin housing; 3) the metal hook may be small in size, so that it gives no sense of discomfort to the bucca or lips and the plaque accumulation can be avoided; 4) the metal hook can be easily bent in such a manner as not to be brought into contact with the gingiva, thereby avoiding gingival inflammation.

In the second invention, the bracket with a hook further comprises a connecting member for connecting the metal body and the hook and the connecting member is embedded in the synthetic resin housing. In other words, when the hook and the metal body are formed as separate pieces and then formed into one-piece unit, it is preferable that the hook is attached to the metal body at the portion embedded in the housing, and the connecting member is not exposed outside the bracket. The word "connecting member" means not only the connecting portion between the hook and the metal body manufactured as separated pieces and then welded to one-piece unit, but also the connecting portion between the hook and the metal body originally formed in one-piece unit.

When the connecting member is located inside the housing, plaque accumulation onto the irregular outer surface of the connecting member can be avoided. In addition, as the connecting member is located inside the synthetic resin housing, a large part of the metal portions become invisible, especially in the case where the synthetic resin housing is milk white color or semi-transparent. Accordingly, the appearance of the bracket as a whole is not deteriorated. Preferably, the hook is attached to the bottom of the metal body.

It is within the scope of the present invention that the hook is attached to the side of the metal body. In this case, however, a force application to the hook may deform the metal body. As a result, the inner space of the metal body which has been precisely determined for engaging an arch wire therein is changed. If the inner space of the metal body is changed, a force applied by the arch wire cannot be properly transferred to the tooth.

Contrary to this, when the hook is attached to the bottom of the metal body, the force application to the hook never changes the inner space of the metal body. Therefore, a force applied by the arch wire can be properly transferred to the tooth, so that accurate treatment is ensured. As described above, the hook may be attached to the side of the metal body.

In general, the hook projects from the synthetic resin housing through one of the wings. When the hook is attached to the side of the metal body, the hook can straightly project from the housing through the wing without the necessity to be bent. Accordingly, the bracket can be simply manufactured.

Preferably, the metal body is configured such that a space of the groove formed therein is enlarged in the middle of the bracket in its plan view.

Unlike the metal body enclosed with flat surfaces only, the metal body formed with an enlarged portion is highly resistive against a bending force. With this structure, even if an orthodontic force is applied to the hook, a deformation of the metal body is negligible, and so is a change in the inner space of the metal body. Therefore, the force applied by the arch wire can be properly transferred to the tooth. In the case of twin-type bracket, when an arch wire is engaged into the groove of the metal body and a fastening wire is tightly put around the wings in this state, the arch wire is pushed down at the enlarged portion. In this manner, the arch wire is firmly fixed to the bracket. By adopting various combination of wings for putting a fastening wire in the twin-type bracket, high performance can be attained during treatment. The metal body is configured such that a depth and a width of the groove formed therein are enlarged in the middle of the bracket in its plan view.

Preferably, the hook is warm colored so that the hook is not conspicuous. In this manner, the appearance of the bracket as a whole is not deteriorated. Examples of the preferable warm color include gold and tooth germ color. Methods for coloring the hook include plating, deposition, anodizing, dip coating and the like.

For example, the hook can be colored a gold color by gold plating. Gold color is a quiet (non-conspicuous) color in a mouth, unlike the silver color of stainless steel, and therefore the appearance of the bracket as a whole is not deteriorated even if the hook is made of metal. As the housing is made of synthetic resin, the portion of the metal hook located inside the housing generates halation by the synthetic resin. Therefore, the portion of the hook inside the housing is not conspicuous.

In addition to the metal plating, there are other methods for coloring the hook such as coloring with pigment or coating with a resin. It is preferable that both the hook and the metal body are colored into a warm color. The coloring of the hook and the metal body is effective to avoid deterioration of the appearance.

As the embedded portions of the metal body and the hook are invisible, there is no problem if the coloring thereof easily peels off. The inner surface of the metal body is brought into contact with the arch wire, and therefore there is a possibility that the coloring peels off at the portions brought into contact with the arch wire. However, the peeling of the coloring causes no problem in this case. This is because the inner surface of the metal body is always behind the arch wire, and therefore is invisible. Therefore, the appearance of the bracket as a whole is not deteriorated. It is desirable that the inner surface of the metal body is not colored in order to ensure that the arch wire can smoothly move inside the metal body. When the inner surface of the metal body is colored, it is preferable that the metal body is colored with a material which generates only a small friction with the arch wire. For example, polytetrafluoroethylene is preferable for coloring the metal body, because it is hard to peel off, and in addition its coefficient of friction is small so that the arch wire can smoothly move inside the metal body.

Preferably, the top of the hook is coated with a synthetic resin. Coated with a synthetic resin, the top of the hook has a mild and soft touch. Even in the case where the gingiva is brought into contact with the top of the hook, the gingiva receives only a small stimulation, and does not become inflamed.

When the synthetic resin coating is flexible, the hook can be bent even if the entire hook projecting from the housing is coated with the synthetic resin. When the synthetic resin coating is not flexible, only the top of the hook is coated with the synthetic resin, so that the hook can be bent. When the hook is coated with a synthetic resin is warm colored, for example colored in ivory, the hook is invisible. Accordingly, the appearance of the bracket as a whole is not deteriorated.

The synthetic resin housing has a wing and the hook projects from the synthetic resin housing through the wing.

The wing is also made of synthetic resin, and the hook projects from the housing through the wings. The connecting portion between the hook and the metal body is consolidated inside the synthetic resin housing. This structure further enhances the fixation of the hook to the housing beyond the attachment of the hook to the metal body. The bracket with a hook may be a twin-type bracket formed with two pairs of wings, or may be a single-type bracket formed with one pair of wing.

Hereinafter, the third invention will be described. According to the third invention, a single-type bracket is provided. The bracket includes a metal body formed with a groove therein adapted for being engaged with an arch wire, and a synthetic resin housing for accommodating the metal body therein such that inner surface of the groove is exposed. The metal body is configured such that a space of the groove formed therein is enlarged in the middle of the bracket in its plan view. As the single-type bracket is smaller in size than the twin-type bracket, it gives no sense of discomfort to the bucca or lips, and the plaque accumulation can be avoided. In addition, the metal body is highly resistive against the bending force, and is not easily deformed when a force is applied thereto.

Hereinafter, the present invention will be further described in detail by way of examples.

EXAMPLE 1

Description of a Bracket Without Hook

Figure 2B:
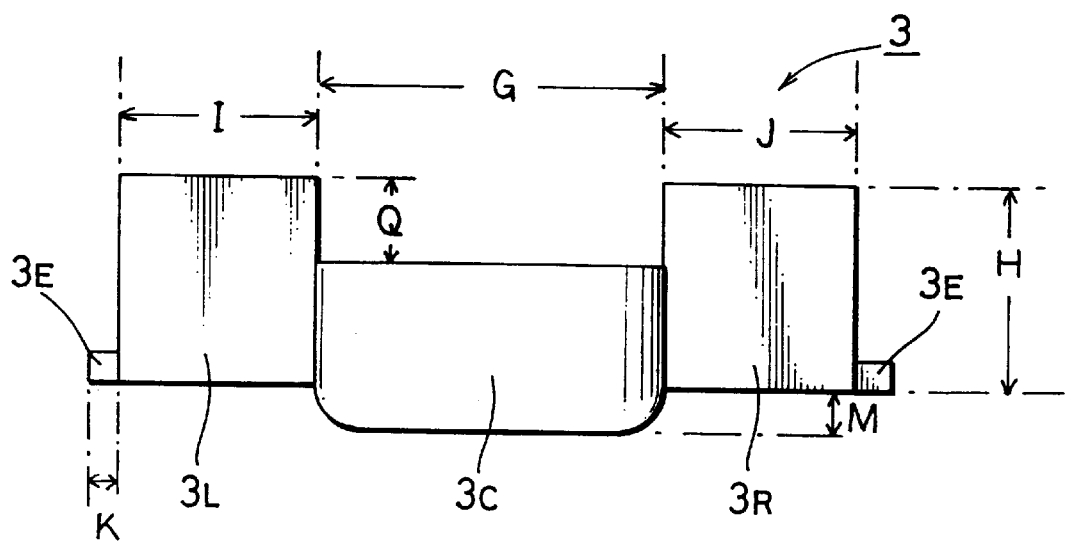
FIG. 2B is a side view of the bracket shown in FIG. 2A.
Figure 3:
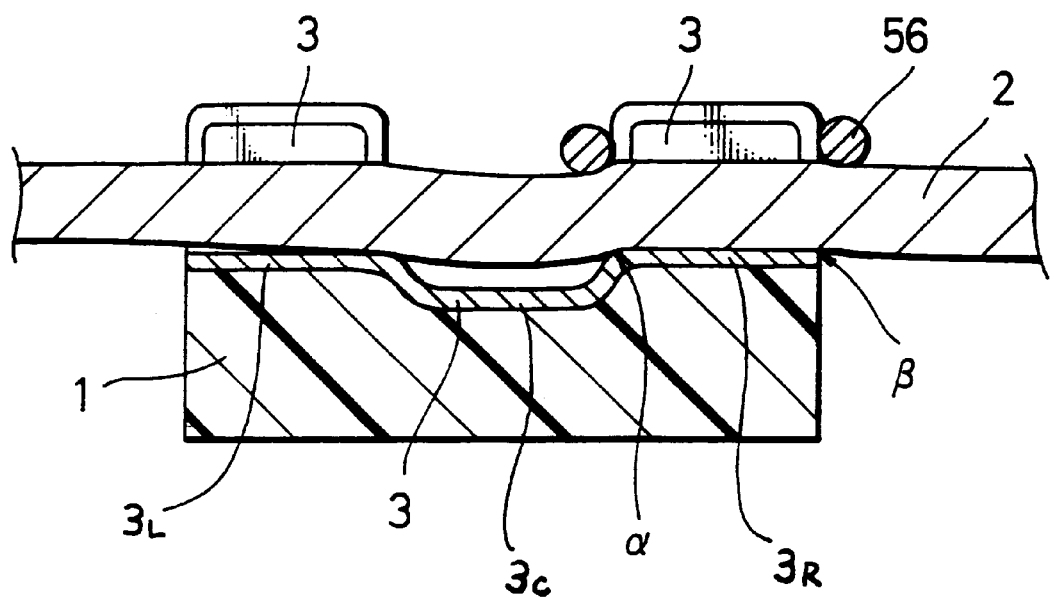
FIG. 3 is a cross-sectional view along the line III—III FIG. 1A.

FIGS. 1A to 1C are diagrams showing a bracket without hook. FIG. 1A is a perspective view illustrating a state where an arch wire 2 is engaged to a metal body of a bracket 1. FIG. 1B is a cross-sectional view taken along the line $I_B$—$I_B$ of FIG. 1A. FIG. 1C is a cross-sectional view taken along the line $I_C$—$I_C$ of FIG. 1A. FIG. 2A is a perspective view showing a metal body 3. FIG. 2B is a side view of the metal body 3. FIG. 3 is a cross-sectional view taken along the line III—III of FIG. 1A. In the description below, the right side of the bracket seen from above is referred to the right side of the bracket, and the left side of the bracket seen from above is referred to the left side of the bracket.

The bracket 1 is a twin-type bracket formed with two pairs of wings $4_{Ru}$, $4_{Rd}$, $4_{Lu}$, $4_{Ld}$. The bracket includes a housing bracket (hereinafter simply referred to as a housing) made of synthetic resin and a metal body 3 formed with a groove therein. The housing is formed with a groove running along its center from one side to the other side in a horizontal direction. The groove is fitted with a metal body 3.

The metal body 3 is formed with a groove, and is configured such that a width and a depth of the groove are enlarged in the middle of the bracket to form an enlarged portion 3C. The left side portion $3_L$ and the right side portion $3_R$ of the metal body 3 form a square-shaped space to which a square-shaped arch wire 2 is engaged with a little clearance. Upon engaging the arch wire 2 to the metal body 3, a fastening wire is put around, for example, the wings $4_{Ru}$, $4_{Rd}$ so as to firmly fix the arch wire 2 to the bracket. In this state, the arch wire gives a force to the tooth at a desirable torque angle. As shown in FIG. 2A, the right and left ends of the bottom surface of the metal body 3 extend beyond the left sides portion $3_L$ and the right side portion $3_R$. When the metal body 3 is accommodated to the housing of the bracket 1, the right and left end surfaces $3_E$, $3_E$ of the metal body 3 are flush with the right and left side surfaces of the housing.

As described above, the metal body 3 is accommodated to the synthetic resin housing. In this case, the inner surface and the end surfaces BE, BE of the metal body 3 are exposed to the outside (see FIG. 1).

Figure 4A:
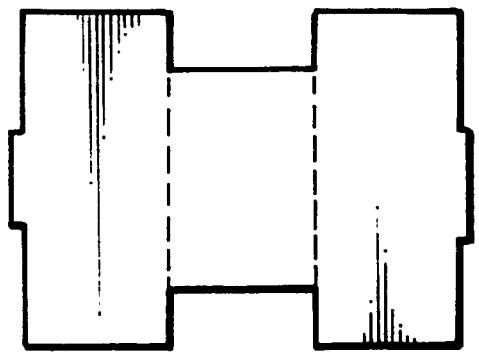
FIG. 4 is a diagram for illustrating the steps of manufacturing a bracket without a hook.
Figure 4B:
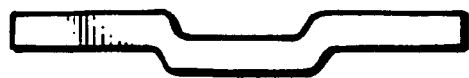
Figures 1, 4C:
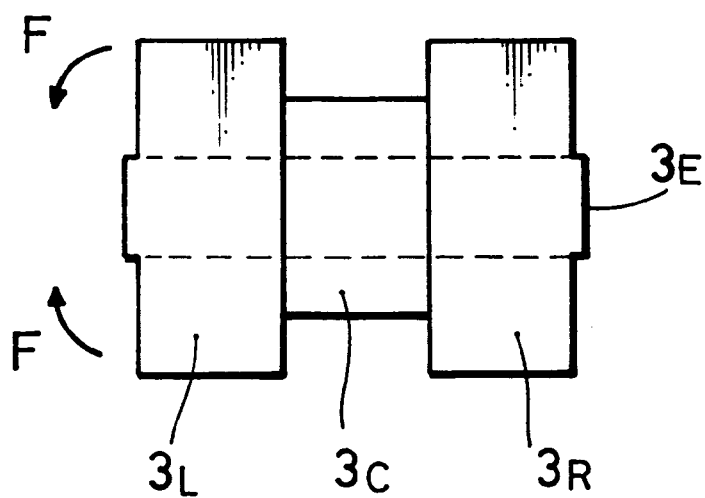
FIGS. 1A to 1C are diagrams showing a bracket without a hook according to Example 1 of the present invention.

In the treatment, the arch wire 2 is engaged with to the metal body 3. In this state, a fastening wire 56 is put around the wings so as to firmly fix the arch wire 2 to the bracket 1. In FIG. 1, the fastening wire 56 is put around the pair of wings $4_{Ru}$, $4_{Rd}$ so as to firmly fix the arch wire 2 to the bracket. As shown in FIG. 1B, at the portion corresponding to the wings $4_{Ru}$, $4_{Rd}$, that is, at the right side portion $3_R$ of the metal body 3, the arch wire 2 is tightly brought into contact with the inner side surface of the metal body 3 so as not to move. Furthermore, as shown in FIG. 1C, the metal body 3 is configured such that a space of the groove formed therein is enlarged in the middle of the bracket (i.e., an enlarged portion 3c of the metal body 3), so that the arch wire 2 is not brought into contact with the inner side surface the metal body 3 at the enlarged portion.

Figure 14A:
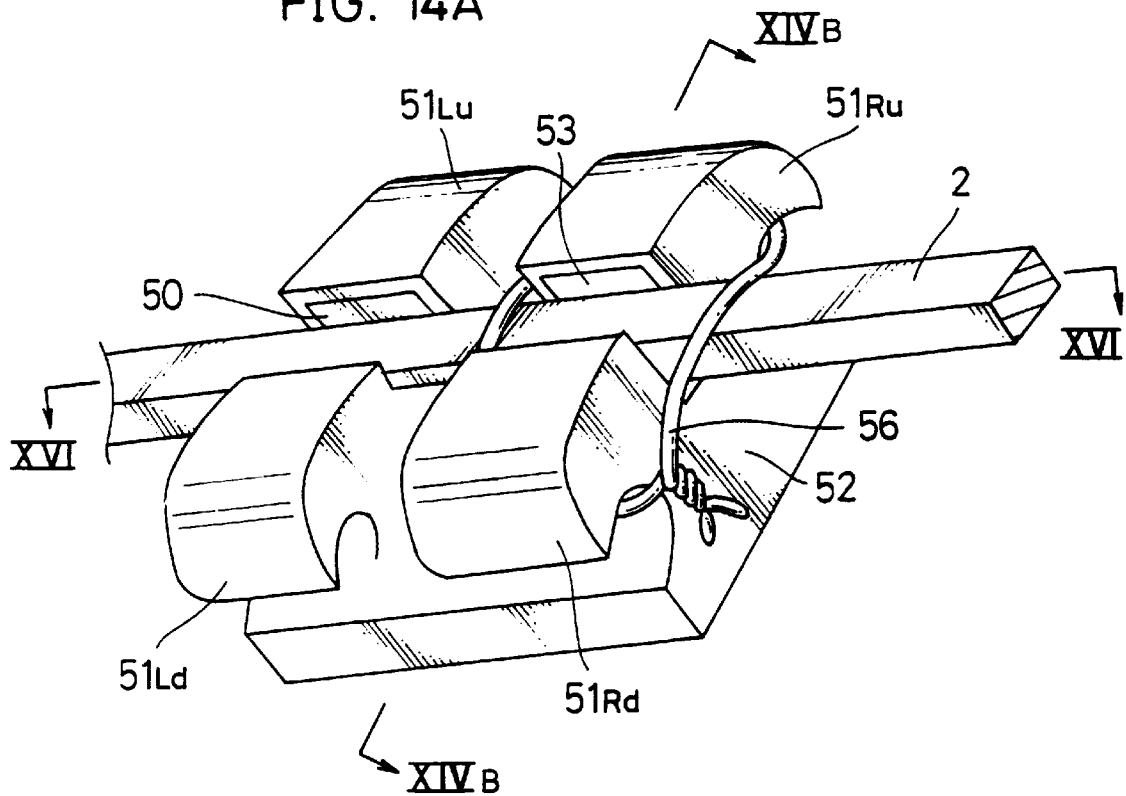
FIG. 14A is a perspective view illustrating a state where an arch wire is fixed to the bracket shown in FIG. 11.
Figure 14B:
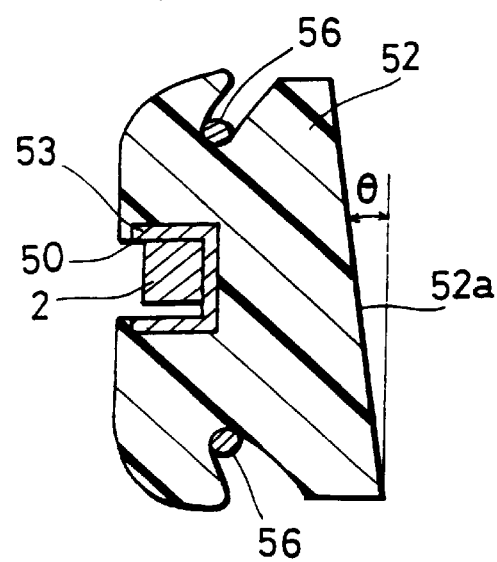
FIG. 14B is a cross-sectional view taken along the line $XIV_B$—$XIV_B$ of FIG. 14A.

The enlarged portion 3c in the middle of the metal throttle 3 is effective for tightly fixing the arch wire 2 to the bracket 1. More specifically, while the arch wire 2 is engaged to the metal body 3, the fastening wire is strongly put around the wings. The arch wire is pushed down at the enlarged portion 3c as shown in FIG. 3. By being pushed down at the wide portion 3c, the arch wire is strongly brought into contact with the metal body 3 at the points α and β in FIG. 3. In this manner, unlike the bracket of Conventional Example 3 (see FIGS. 11, 12, and 14), the arch wire 2 is firmly supported at the points α and β, thereby being tightly fixed to the bracket 1 without sliding inside the groove of the metal body 3. Even if only one pair of wings is used as shown in FIG. 1, the arch wire 2 can be firmly fixed to the bracket 1. With this structure, various combinations of the wings $4_{Ru}$, $4_{Rd}$, $4_{Lu}$, $4_{Ld}$ can be applicable for winding the fastening wire 56, so that the tooth can be moved to any desirable direction. The twin-type bracket with this structure exhibits excellent performance in the orthodontic treatment.

In the orthodontic treatment, there may be steps in which the arch wire is required to smoothly move inside the groove of the metal body. The bracket 1 of Example 1 can be preferably used in such steps. As the arch wire 2 is not brought into contact with the inner surface of the groove of the metal body 3 at the enlarged portion 3c, the contact area between the arch wire 2 and the metal body 3 is small and the friction resistance therebetween is reduced. Therefore, the arch wire can smoothly move inside the groove of the metal body 3, so that an effective treatment can be conducted.

Figure 13:
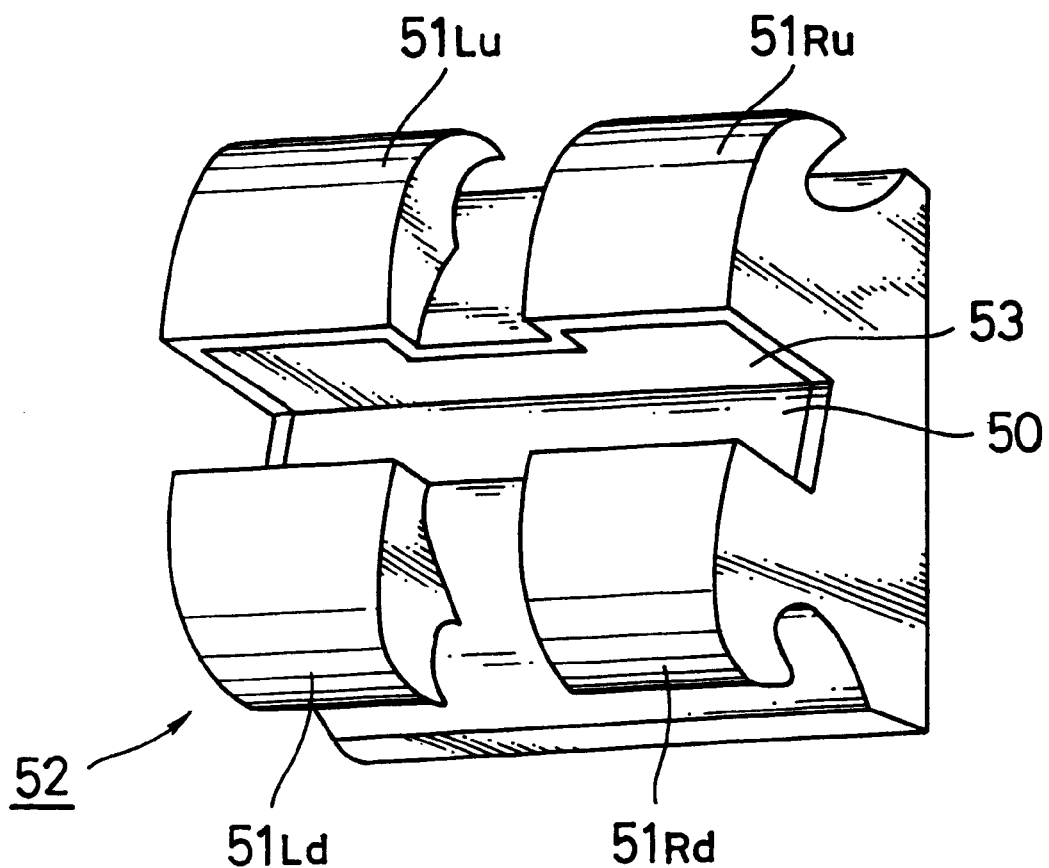
FIG. 13 is a perspective view showing a twin-type bracket without hook according to Conventional Example 3.
Figure 15:
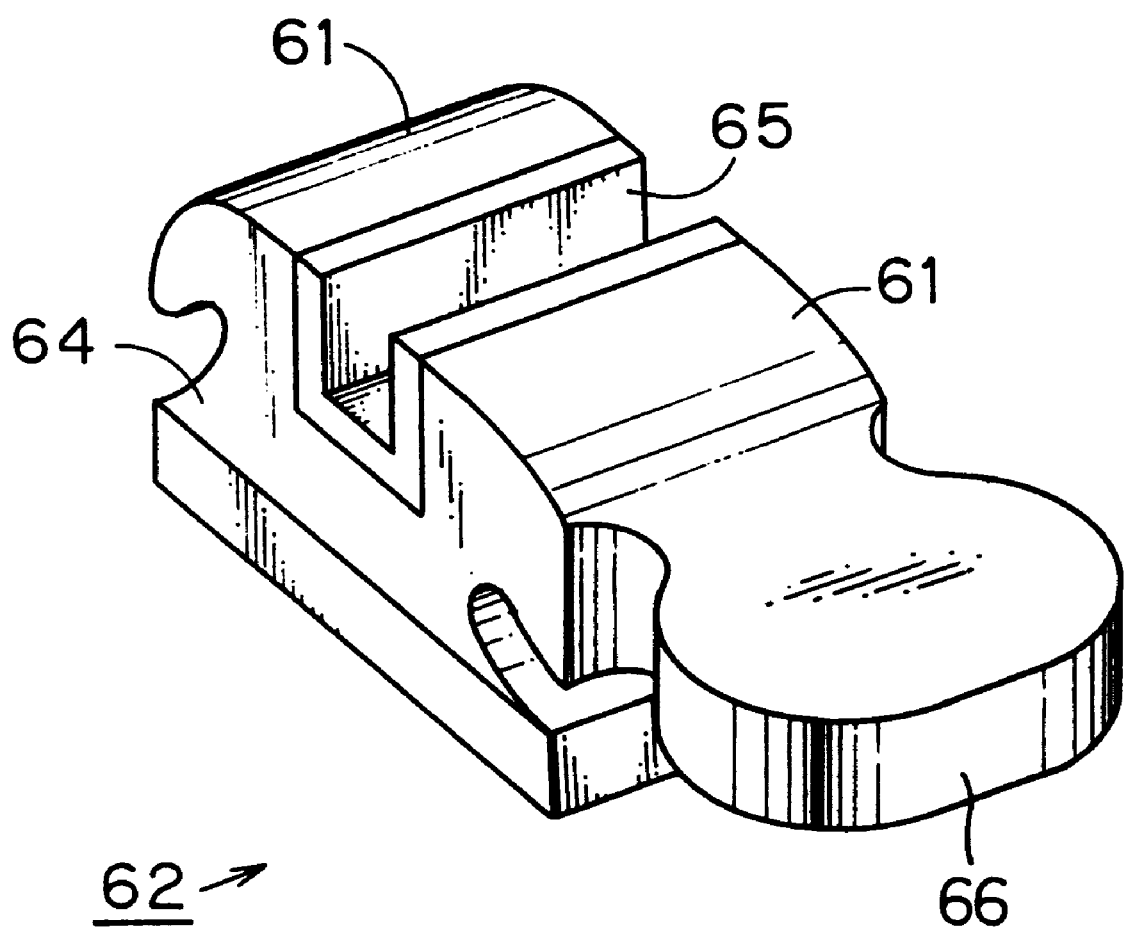
FIG. 15 is a perspective view showing a single-type bracket with a hook according to Conventional Example 3.

In addition, the metal body 3 configured such that a space of the groove formed therein is enlarged and is highly resistive against bending forces, and therefore is hard to be deformed, unlike the metal bodies 53, 65 of Conventional Example 3 enclosed with only flat surfaces (FIGS. 13 and 15). Therefore, the metal body 3 is kept in its initial shape.

With the enhanced strength, the metal body 3 may have a smaller thickness. If the housing of the bracket 1 is made of synthetic resin and therefore is transparent, there may be a possibility that the metal body 3 embedded in the housing is visible from the outside. However, when the metal body has a small thickness, the metal body is barely visible from the outside, thereby avoiding deterioration of its appearance.

Figure 16:
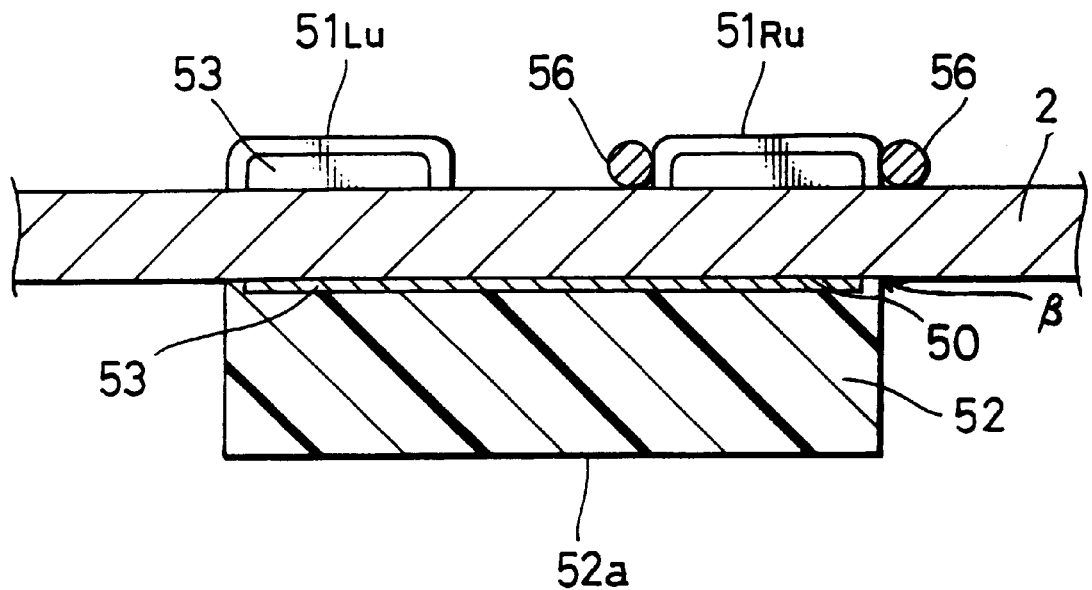
FIG. 16 is a cross-sectional view taken along the line XVI—XVI of FIG. 14A.

In Example 1, the metal body 3 has end surfaces $3_E$, $3_E$ extending beyond the right side portion $3_R$, and the left side portion $3_L$ so as to be flush with the side surfaces of the housing when accommodated (see FIG. 3). If the metal body is short and its side surfaces are not flush with the side surfaces of the housing, the portions of the groove of the synthetic resin housing not covered with the metal body may be worn out in contact with the arch wire, as was the case in the prior art (see FIG. 16). As a result, the housing may be deformed at the portion of the groove uncovered with a metal body, and a desirable and accurate treatment cannot be conducted. Contrary to this, in Example 1, as the metal body 3 has end surfaces $3_E$, $3_E$ extend beyond the right side portion $3_R$, and the left side portion $3_L$ so as to be flush with the side surfaces of the housing when accommodated, the arch wire 2 is brought into contact with the metal body 3 at the point β in FIG. 3. Therefore, the housing may be deformed at the portion uncovered with a metal body. In the above-description, the metal body 3 is formed in such a structure that its end surfaces $3_E$, $3_E$ are flush with the side surfaces of the groove of the housing when the metal body 3 is accommodated to housing; however, the metal body 3 may be shorter than the groove of the housing to some extent. Even if the metal body 3 is shorter than the groove of the housing to some extent and the end portions of the groove of the synthetic resin housing are exposed to some extent, there is no fear that the end portions are worn out. Therefore, there is no serious influence to the orthodontic treatment.

Figures 2, 4C:
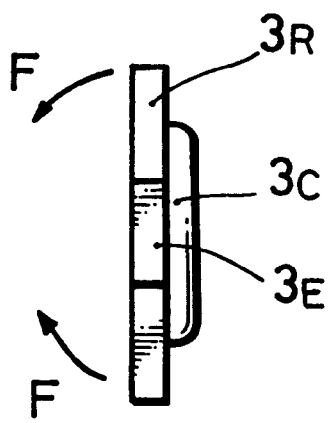

Referring to FIG. 2, an example of the size of the metal body 3 is as follows: thickness: 0.5 mm; size N: 0.46 mm; size P: 0.1 mm; sizes I and J: 0.83 mm; the size G: 1.0 mm; size K: 0.18 mm; size H: 0.95 mm; size M: 0.1 mm; and size Q: 0.3 mm. In addition, an example of the size of the bracket 1 is described as follows: the size in the horizontal direction: 3.5 mm; the size of the widest portion in the perpendicular direction: 3.0 mm; and the thickness of the thickest portion (height): 2.05 mm. Each part of the bracket 1 is formed to have a groove and torque angle desirable for the treatment. It should be understood that the bracket and the groove are not limited to the above sizes.

Next, an example of the method for manufacturing the bracket of the Example 1 will be described. FIGS. 4A to 4C-2 are diagrams illustrating an example of steps of manufacturing the metal body 3 (see FIG. 2). First, as shown in FIG. 4A (a plan view), a flat metal plate is cut into a substantial H-shape. Then, the H-shaped plate is concaved along the dashed lines shown in FIG. 4A in a depth direction as shown in FIG. 4B (a side view) to form an enlarged portion 3c. Then, as shown in FIGS. 4C-1 (a plan view) and 4C-2, the metal plate is bent along the dashed lines to form a substantial U-shape. As a result, a metal body 3 is obtained. Thus-obtained metal body 3 made of one plate is hard to be broken and can be produced by simple steps. The metal body 3 may be produced by bending each portion one by one, or may be produced by bending all the portions at the same time by a press operation.

Then, the obtained metal body 3 is placed at a specific position of the mold for injection molding of the synthetic resin housing. While the housing is injection-molded, the metal body 3 is accommodated thereto (hereinafter, referred to as an insert molding). Unlike the metal body 53 of Conventional Example 3 (see FIG. 13) enclosed with flat surfaces only, the metal body 3 of Example 1 is formed with a groove having an enlarged portion 3c in the middle. If the groove of the housing is also formed with an enlarged portion in the middle in the insert molding, the metal body 3 can be easily accommodated in the housing by engaging the enlarged portion 3c of the metal body to the enlarged portion of the housing. In this manner, the positioning of the metal body 3 to the housing is facilitated.

In addition to the sheet metal plating described above, the metal body 3 can be manufactured by casting or by metal powder metallurgy. In addition to the insert molding described above, the metal body 3 can be accommodated to the housing by press fitting.

As the metal body 53 of Conventional Example 3 is enclosed with flat surfaces only without an enlarged portion (see FIG. 13), the metal body 53 is not sufficiently accommodated to the housing and may slip off the housing. In contrast, the metal body 3 of the present invention has an enlarged portion in the middle, and the enlarged portion serves as a stopper to prevent the metal body 3 from slipping off the housing.

EXAMPLE 2

Figure 5:
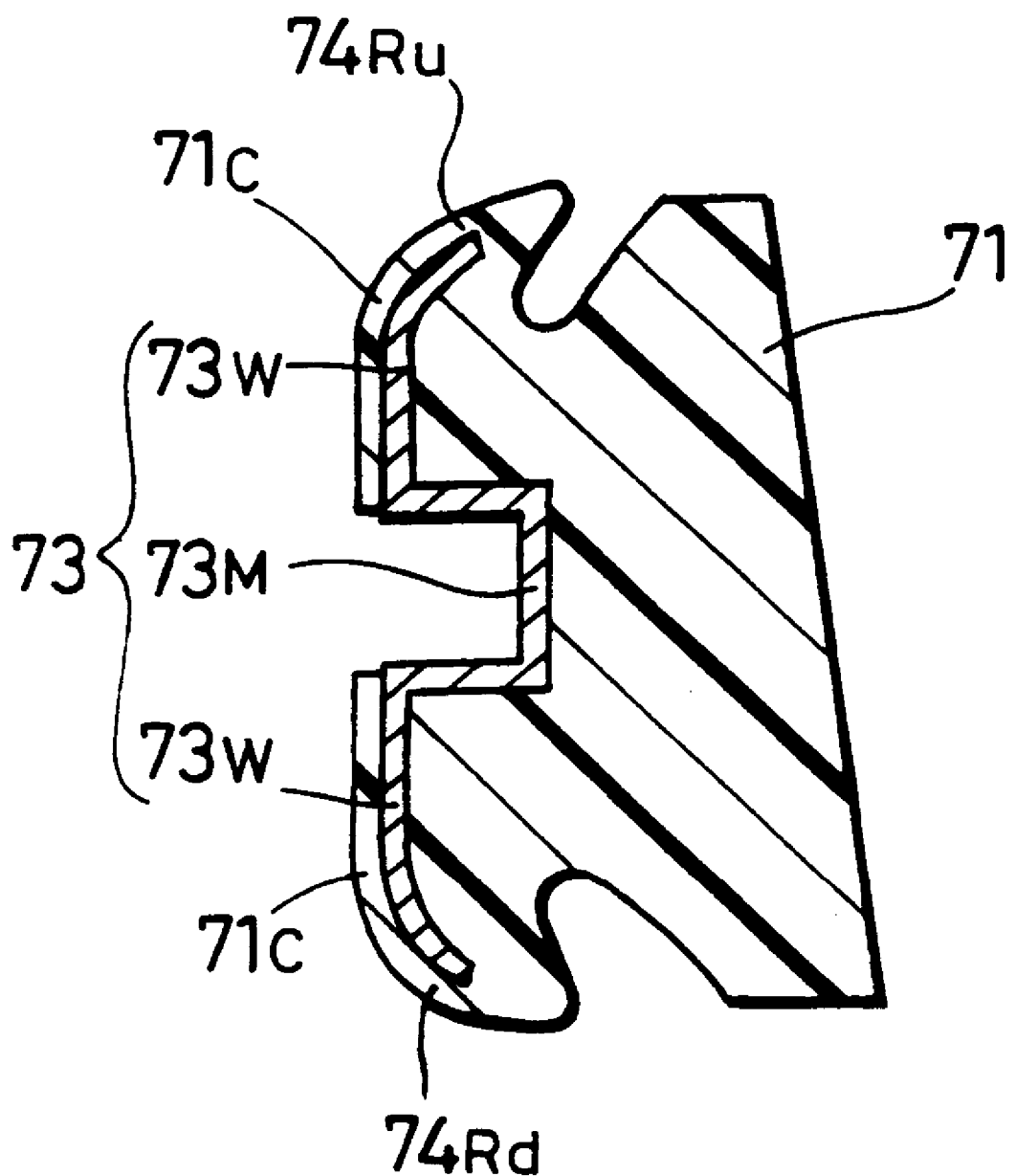
FIG. 5 is a cross-sectional view showing a bracket without a hook according to Example 2 of the present invention.

FIG. 5 is a cross-sectional view showing a bracket 71 without a hook for an orthodontic appliance taken along the line from the wings $74_{Ru}$ to $74_{Rd}$ of FIG. 1B (in FIG. 5, the arch wire and the fastening wire are not shown). The bracket 71 includes a housing made of synthetic resin and a metal body 73. The metal body 73 includes a groove portion $73_M$ and wing core portions $73_W$. The groove portion $73_M$ is positioned to the groove of the housing. The wing core portions 73W, 73W are embedded in the wings $74_{Ru}$, $74_{Rd}$. As is the case of Example 1, the groove portion $73_M$ has an enlarged portion in the middle.

In the orthodontic treatment, as is the case of Example 1 shown in FIG. 1, the arch wire (not shown) is engaged to the groove portion $73_M$, and then, a fastening wire is put around the wings $74_{Ru}$, to $74_{Rd}$ to tightly fix the arch wire to the bracket 71. The wing core portions $73_W$, $73_W$ are embedded in the wings $74_{Ru}$, $74_{Rd}$ and are covered with cover portions $71_c$, $71_c$. The cover portions $71_c$, $71_c$ are made of synthetic resin, and the wing core portions $73_W$, $73_W$ are not exposed to the outside. When the cover portion $71_C$ made of synthetic resin is transparent or semi-transparent, the wing core portions $73_W$, $73_W$ are visible through the cover portions $71_c$, $71_c$. In this case, the wing core $73_W$ is colored, for example, milk white so that the wing core portions $73_W$, $73_W$ are invisible from the outside. If the metal which is colored is exposed to outside without being provided with cover portions, it is rather noticeable because it is not transparent. However, in Example 2, the wing core portions $73_W$, $73_W$ made of metal are covered with the cover portions 71C, 71C which are made of synthetic resin and are transparent or semi-transparent. With this structure, the bracket gains transparency and does not deteriorate the appearance of the bracket as a whole. In addition, the wing core portions $73_W$, $73_W$ enhance the strength of the wings $74_{Ru}$, $74_{Rd}$.

According to Example 2, the bracket without hook includes a housing made of synthetic resin, and therefore the housing may be milk white color, semi-transparent, or transparent. Such a bracket does not deteriorate the appearance of the bracket as a whole during the treatment. When the twin-type bracket includes a metal body formed with a groove having an enlarged portion, a bracket having high strength and high performance can be attained during the treatment.

EXAMPLE 3

Bracket With a Hook

Figure 6A:
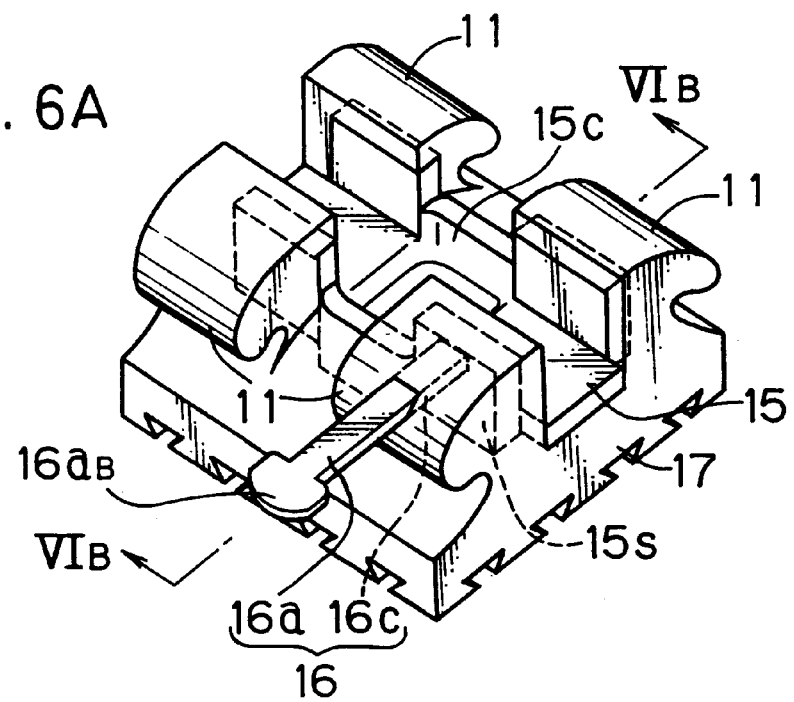
FIG. 6 is a diagram showing a bracket with a hook according to Example 3 of the present invention.
Figure 6B:
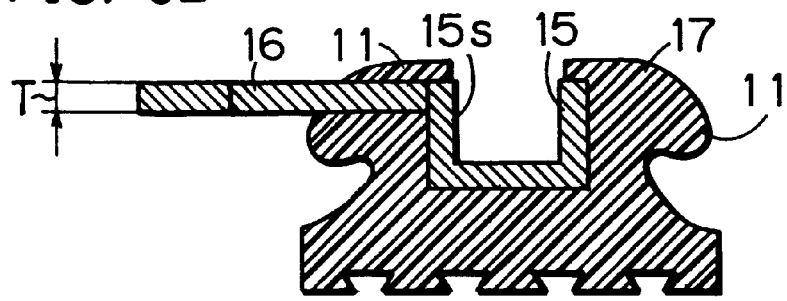
Figure 6C:
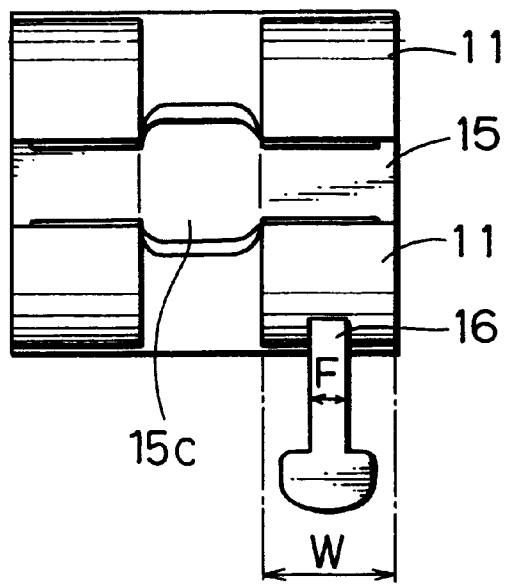
Figure 7:
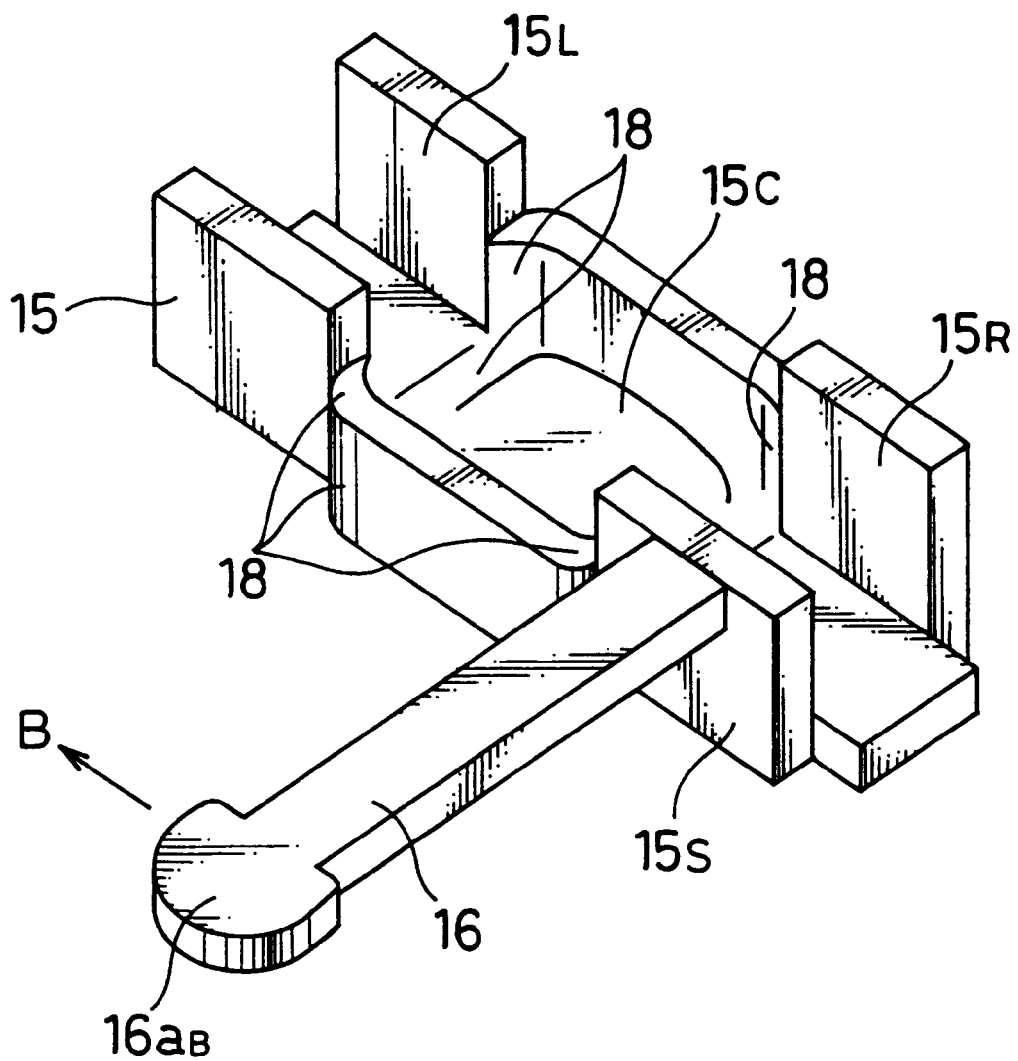
FIG. 7 is a perspective view showing a metal body and a hook of the bracket according to Example 3 of the present invention.

FIG. 6A is a perspective view showing a bracket with a hook. FIG. 6B is a cross-sectional view showing the bracket taken along the line $VI_B$—$VI_B$ of FIG. 6A. FIG. 6C is a plan view showing the bracket seen from the bucca and lip side. FIG. 7 is a perspective view showing a metal body and a hook of Example 3.

The bracket of Example 3 is a twin-type bracket formed with two pairs of wings 11. The bracket 17 includes a housing 17 made of transparent synthetic resin, and a metal body 15. The metal body 15 is formed with a groove adapted to be engaged with an arch wire, and is accommodated to the housing 17. The metal body 15 is configured such that a width and a depth of the groove formed therein is enlarged in the middle of the bracket 17, and the inner surface of the groove is exposed to the outside.

The metal body 15 is provided with a metal hook 16. The hook 16 is attached to the side of the metal body 17 by welding, and the connecting portion therebetween is embedded in the housing 15. The hook 16 projects from the housing 17 through the wing 11 (FIGS. 6A and 6B) in a direction perpendicular to the length of the groove. The top of the hook 16 projecting through the wing 11 is referred to a hook portion 16a, and the portion of the hook 16 embedded in the housing 17 is referred to as a hook-embedded portion 16c.

The hook 16 is gold-plated. The hook 16 is in the form of flat stick (a substantial square column), and is thin and small. The top of the hook portion 16a is enlarged (hereinafter, referred to as a button $16a_B$) so that a rubber ring can be easily engaged thereto.

The width F of the hook 16 is small as compared with the width W of the wing 11. For example, when the width W of the wing 11 is 1.2 mm, the width F of the hook 16 is 0.5 mm, and the thickness I of the hook 16 is 0.3 mm (FIGS. 6B and 6C).

In the orthodontic treatment, the arch wire is engaged to the groove of the metal body 15. In this state, a fastening wire is put around the wings 11, so that the arch wire is tightly fixed to the bracket 17, thereby giving a force to the tooth. Simultaneously, a rubber ring is engaged to the button $16a_B$ of the hook portion 16a, thereby also giving another force to the tooth. Depending on the necessity, there may be steps where only an arch wire is used and a rubber ring is not used, or there may be steps where only a rubber ring is used and an arch wire is not used.

As the hook portion 16a is small in size. It gives less sense of discomfort to the bucca and lips, whereby the patient feels a good sense of fitting. In addition, the plaque accumulation can be avoided. Furthermore, as the hook portion 16a is made of metal, it can be bent. The contact between the hook portion 16a and the gingiva can be prevented by bending the hook portion 16a. As the hook 16 (and the hook portion 16a) is strongly attached to the metal body 15, the hook portion 16a never detaches therefrom.

Furthermore, according to Example 3, the metal body 15 is formed with a groove having an enlarged portion. With the enlarged portion, the metal body 15 has high resistance to the force applied thereto. When a force is applied to the metal body 15 through the hook portion 16a by engaging a rubber ring, the metal body 15 is mot easily deformed. The boundary 18 between the center portion 15c and the right side portion 15R, and between the center portion 15c and the left side portion 15, is directed in a direction different from the direction along which the arch wire is inserted (that is, the boundaries are directed in a vertical direction). Therefore, when a force is applied in a direction B in FIG. 7, the boundaries 18 receive the force along the direction perpendicular to their extending direction. With this structure, a metal body 15 has high resistance to force and is never deformed.

In addition, the metal body 15 is formed with an enlarged portion 15c. When the arch wire is engaged to the metal body 15, the arch wire is not brought into contact with the metal body 15 at the enlarged portion 15c. Therefore, the contact area between the arch wire and the groove of the metal body 15 is reduced so that the friction resistance is small. As a result, an arch wire can smoothly move inside the groove of the metal body 15. Thus-formed bracket can be effectively used in a treatment where the arch wire is required to smoothly move in the groove.

The hook is gold colored by gold-plating. Gold color is a warm color close to the teeth color. When seen through the transparent housing made of synthetic resin, the gold hook generates halation and is hard to be distinguished with the milk white color of the tooth. In addition, the hook portion 16a projecting from the housing through the wing is gold colored, and therefore, is not conspicuous.

EXAMPLE 4

Figure 8:
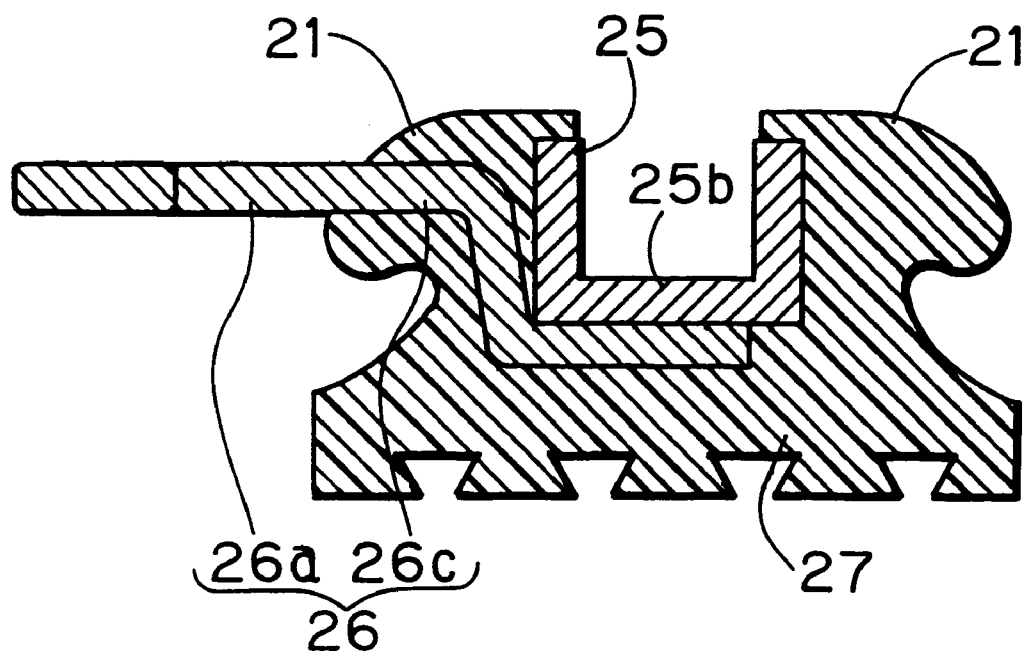
FIG. 8 is a cross-sectional view showing a bracket with a hook according to Example 4 of the present invention.

FIG. 8 is a cross-sectional view showing a bracket with a hook taken along the line perpendicular to the insertion direction of the arch wire. FIG. 8 corresponds to FIG. 6B. The bracket of Example 4 has a same structure as that of the bracket of Example 3 except that in Example 4 the hook 26 is attached to the bottom 25b of the metal body 25 by welding. As in Example 3, the hook 26 projects from the housing 27 through a wing 21.

In Example 4, as is the case of Example 3, the hook portion 26a (i.e., the portion which projects from the housing) is small in size. Therefore, the hook portion 26a gives less sense of discomfort to the bucca and lips, and the plaque accumulation can be prevented. In addition, as the hook portion 26a is made of metal, it can be bent.

EXAMPLE 5

Figure 9:
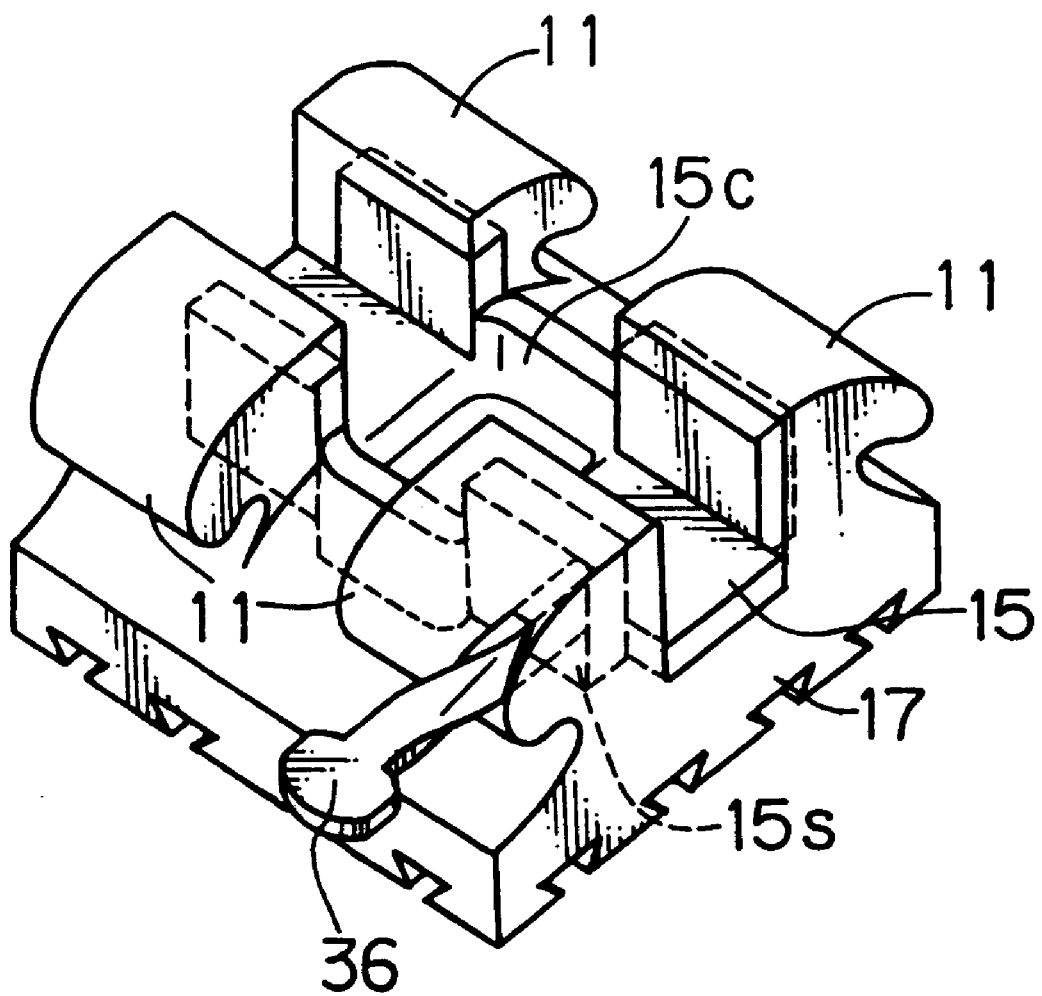
FIG. 9 is a perspective view showing a bracket with a hook according to Example 5 of the present invention.

FIG. 9 is a perspective view showing a bracket with a hook according to Example 5. Whereas in Example 3, a bracket projects from the housing through the wings and straightly extends as shown in FIG. 6, in Example 5, the bracket projects from the housing through the wing and extends while being twisted by about 90°. As the hook 36 in the form of flat stick is twisted in the vicinity of the connecting portion between the metal body 15 and the hook 36, its thinnest dimension is seen from the front. Therefore, the hook 36 is not conspicuous even if the housing is transparent.

Next, an example of the method for manufacturing the metal body 15 and the hook 36 according to Example 5 will be described. FIGS. 10A to 10E are diagrams illustrating the steps of manufacturing the metal body 15 and the hook 36. First, a flat metal plate is cut into a shape shown in FIG. 10A (a plan view). Then, the plate is concaved along the dashed lines shown in FIG. 10A to form an enlarged portion (FIG. 10B, showing a metal plate seen from the bottom). Then, the plate is bent along dashed lines in a direction shown by an arrow G in FIGS. 10C-1 (a plan view) and 10C-2 (a right side view) to form a U-shape. After that, the hook 36 is bent in a direction shown by an arrow H in FIG. 10D (a plan view), and then is twisted in a direction shown by an arrow A in FIG. 10E (a plan view). As a result, a metal body 15 is obtained.

In the treatment, brackets with a hook or brackets without hook are used in combination.

EXAMPLE 6

Bracket Without a Hook

Figure 11A:
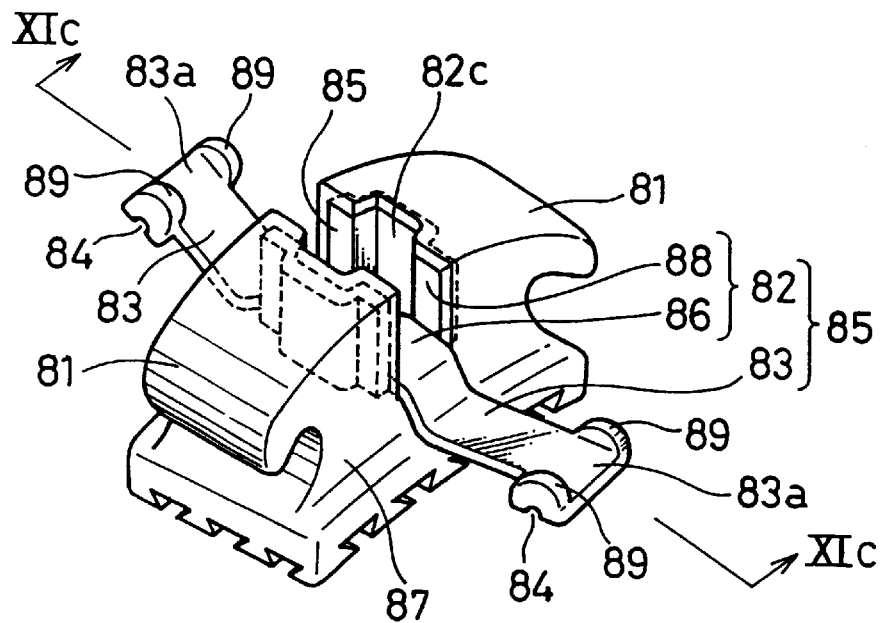
FIG. 11A is a perspective view showing a bracket without a hook according to Example 6.
Figure 11B:
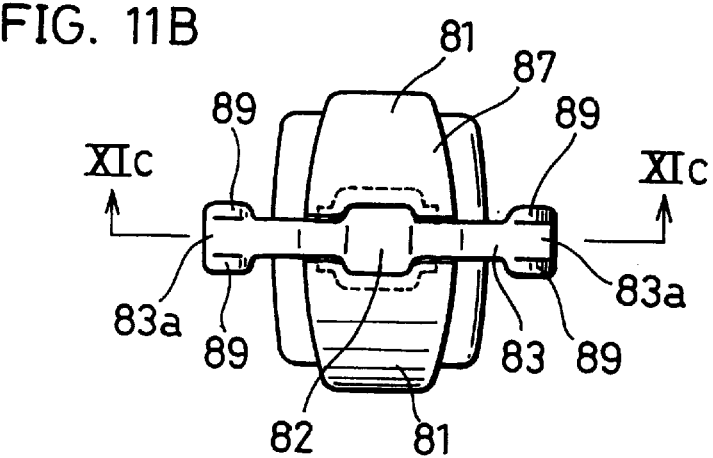
FIG. 11B is a plan view thereof.
Figure 11C:
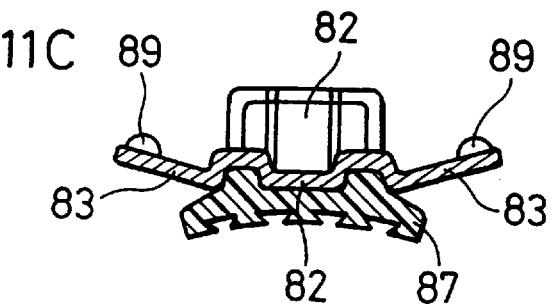
FIG. 11C is a cross-sectional view taken along the line XIc—XIc of FIGS. 11A and 11B.

FIG. 11A is a perspective view showing a bracket without a hook according to Example 6. FIG. 11B is a plan view thereof. FIG. 11C is a cross-sectional view thereof taken along the line XIc—XIc of FIGS. 11A and 11B.

The bracket is in a single type including a metal body 85 and a transparent synthetic resin housing 87 for accommodating the metal body therein. The synthetic resin body 87 is formed with a pair of wings 81. The metal body 85 is formed with a groove 82 therein adapted for being engaged with an arch wire and an extended portion 83 extending from the bottom surface 86 of the metal body 85. The metal body 85 is entirely gold-plated. The metal body 85 is accommodated in the synthetic resin housing 87 in such a manner that the inner surface of the groove 82 is exposed, and the extended portion 83 extends from the bottom surface 86 of the metal body 85 beyond the synthetic resin body 87.

As is the case of Examples 1 to 5, the metal body 85 is configured such that a center portion 82c of the groove 82 formed therein is enlarged in the middle of the bracket in its plan view. In other words, the center portion 82c has a bottom surface 86 concaved in a depth direction and a side wall 88 concaved in a width direction.

An arch wire is supported by the groove 82 and the extended portion 83. The extended portion 83 is configured such that, when seen from its side as shown in FIG. 11C, it goes down the tooth side to a height lower than the bottom surface 86 at the end of the bottom surface 86, and in turn, goes up toward the buccal side at a distant end portion 83a of the extended portion 83. The extended portion 83 has a width equal to or larger than the width of a square-shaped arch wire used in a precise treatment step. On one surface of the distant end portion 83a with which an arch wire is engaged, a pair of projections 89 is provided. The interval between the pair of projections 89 is equal to or relatively larger than the width of the square-shaped arch wire. The other surface of the distant end portion 83a is concaved to form a recess 84 at the position corresponding to the projections 89.

When an arch wire is engaged with the metal body 85 in the groove 82 and the extended portion 83, the arch wire is supported to be brought into contact with the non-concaved portion (i.e., the portion other than the center portion 82c) of the groove 82, and the distal end portion 83a of the extended portion 83. As the bracket of Example 6 is formed with the extended portion 83, it can apply a force to a tooth under excellent control even when the bracket is a single wing type.

In Example 6, an arch wire is prevented from dropping away from the extended portion 83 by being guided by the projections 89. In addition, as the extended portion 83 has substantially the same width as the arch wire, the extended portion 83 is almost entirely hidden behind the arch wire. Therefore, the appearance of the bracket as a whole is not deteriorated.

When a fastening wire is put around the distal end portions 83a through the recess 84 in a state where the metal body is engaged with an arch wire, the fastening wire is held at the recess 84 without shifting therefrom along a lengthwise direction of the extended portion 83. Therefore, an arch wire can be firmly fixed to the bracket.

As is the case of Examples 1 to 6, the metal body 85 has a wider center portion 82c formed in the middle of the groove 82. With this arrangement, the metal body 85 has high strength and is not easily deformed.

EXAMPLE 7

Figure 12A:
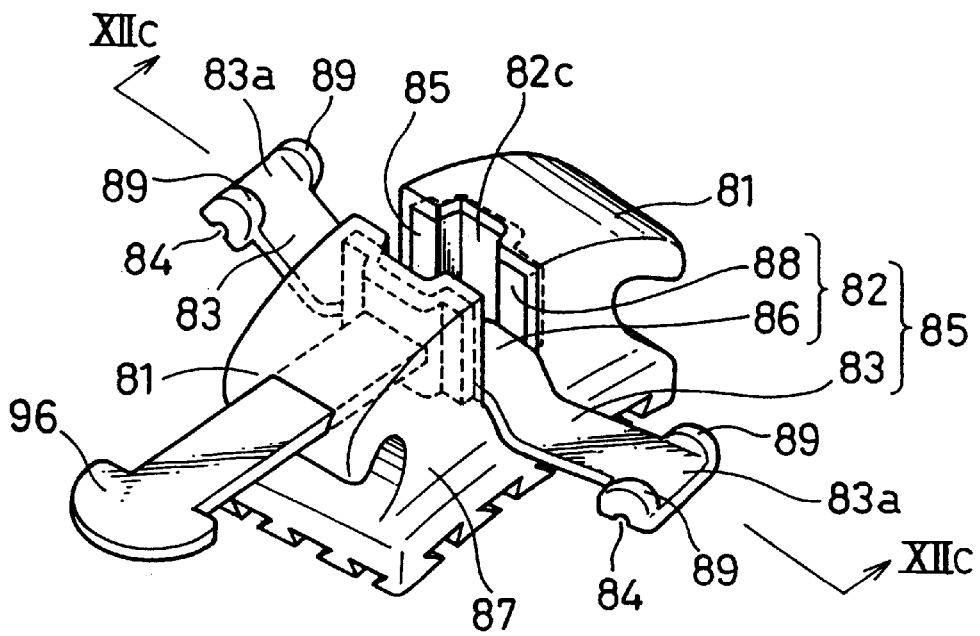
FIG. 12A is a perspective view showing a bracket without a hook according to Example 7.
Figure 12B:
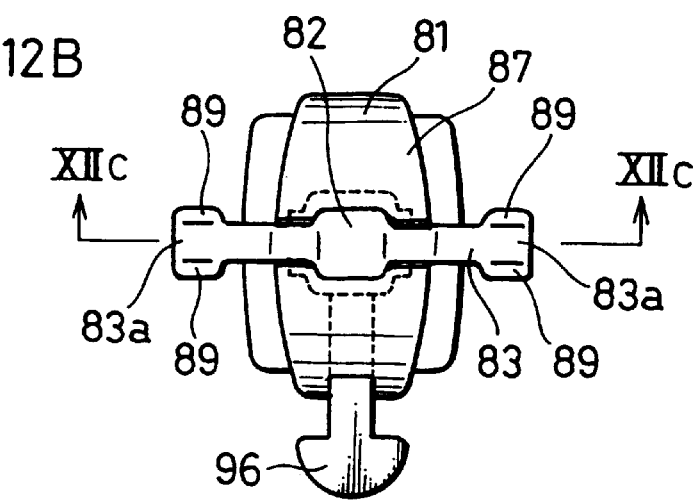
FIG. 12B is a plan view thereof.
Figure 12C:
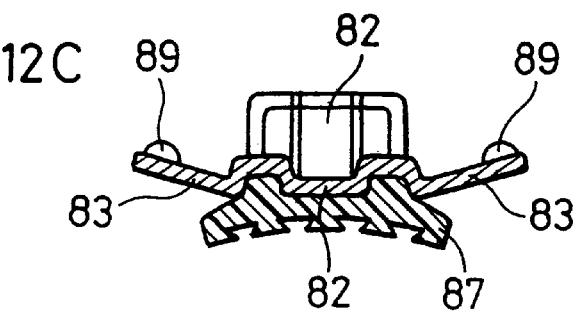
FIG. 12C is a cross-sectional view taken along the line XIIc—XIIc of FIGS. 12A and 12B.

FIG. 12A is a perspective view showing a bracket without a hook according to Example 7. FIG. 12B is a plan view thereof FIG. 12C is a cross-sectional view thereof taken along the line XIc—XIc of FIGS. 12A and 12B.

A bracket of Example 7 is a single-type bracket and has a same structure as of Example 6, except that the bracket of Example 7 has a hook 96. The hook 96 is welded to the side surface 88 of the groove 82 of the metal body 85, and the top end thereof projects from a synthetic rein housing 87 through a wing 81. As is the case of Examples 1 to 6, the hook is made of metal, and therefore, can be small in size and can be bent. Although the bracket is in a single wing form, it can effectively apply a force to a tooth without deterioration of the appearance of the bracket as a whole.

In an orthodontic treatment, brackets with hooks and brackets without hooks, and single-type brackets and twin-type brackets are used in combination.

In Examples 1 to 7, the metal bodies 3 and 15 are formed with a groove having the enlarged portions 3c and 15c respectively, whose width and depth are enlarged. However, the present invention is not limited to this structure. For example, the metal body may be formed with a groove having an-enlarged portion whose depth is enlarged and width is not enlarged.

Examples of material comprising the metal body include metals or alloys such as stainless steel, titanium or their alloys which do less or no harm to human body, and the like. Examples of synthetic resins comprising the housing of the bracket include engineering plastic having high toughness such as polycarbonate, polysulfone, acrylic resin, and the like.

It is common that the housing is made of synthetic resin containing fabrics. In the present invention, the housing is made of synthetic resin containing fabrics.

The synthetic resin housing may be transparent, semitransparent, or milk white color. In the case where the housing is semi-transparent or milk white color, the hook-embedded portions 16, 26c become invisible from the outside, whereby the appearance of the bracket as a whole becomes more natural.

In Examples 1 to 7, the metal body and the hook are attached to each other by welding; however, other methods may be employed such as the attachment by an adhesive, one-piece molding (welding, powder injection molding (MIM), press operation and the like). In Examples 1 to 7, the hook is in the form of flat stick; however, the hook may have other shapes such as a circular cylinder.

In Examples 3, 5, and 7 the hook is attached to the metal body at the position corresponding to one of the wings of the housing; however, the hook may be attached to the metal body at another portion, for example a portion corresponding to an enlarged portion (an enlarged portion 15c of the housing 15).

In Examples 1 to 7, the metal body is formed with a groove having an enlarged portion; however, the groove may not have an enlarged portion and the metal body may be enclosed with flat surfaces only.

Although the present invention has been fully described by way of examples with reference to the accompanied drawings, it is to be understood that various changes and modifications will be apparent to those skilled in the art. Therefore, unless otherwise such changes and modifications depart from the scope of the invention, they should be construed as being included therein.

What is claimed is:

1. An orthodontic bracket adapted for being engaged with an arch wire, comprising:

a metal body having a groove to be engaged with the arch wire;

a synthetic resin housing securable to a tooth and accommodating the metal body therein such that a substantial area of an inner surface of the metal groove is exposed;

said metal body has an extended portion extending in a first direction from a bottom surface of the groove and the extended portion has a remote end provided with a projection on a lateral side with respect to the first direction, on a side where the arch wire is placed.

2. The orthodontic bracket according to claim 1, wherein said projection has an upward convex arc shape.

3. The orthodontic bracket according to claim 1, wherein a remote end of said projection is provided with a pair of projections.

4. The orthodontic bracket according to claim 3, wherein said projection is provided on lateral sides of the extended portion.

5. The orthodontic bracket according to claim 1, wherein the extended portion is configured such that its width at the remote end is wider than that closer to the bottom surface of the metal body.

6. The orthodontic bracket according to claim 1, wherein the extended portion is bent at around the bottom surface of the metal body towards a point away from a plane including the bottom surface of the groove.

7. The orthodontic bracket according to claim 1, wherein the metal body, having an exposed bottom surface and exposed side surfaces, has substantially a U-shape in cross section and has a wider space at an exposed middle portion in the metal body in an arch wire extending direction.

8. The orthodontic bracket according to claim 7, wherein a distance between side surfaces of the groove of the metal body is wider at a middle portion of the metal body in an arch wire extending direction.

9. An orthodontic bracket adapted for being engaged with an arch wire, comprising:

a metal body having a groove to be engaged with the arch wire;

a synthetic resin housing securable to a tooth and accommodating the metal body therein such that a substantial area of an inner surface of the metal groove is exposed;

said metal body has an extended portion extending from a bottom surface of the groove and the extended portion has a remote end provided with a projection on a side thereof where the arch wire is placed, wherein the metal body, having an exposed bottom surface and exposed side surfaces, has substantially a U-shape in cross section and has a wider space at a middle portion in the metal body in an arch wire extending direction, wherein the bottom surface is further recessed at a middle portion of the metal body in an arch wire extending direction.

10. An orthodontic bracket adapted for being engaged with an arch wire, comprising:

a metal body having a groove to be engaged with the arch wire;

a synthetic resin housing securable to a tooth and accommodating the metal body therein such that a substantial area of an inner surface of the metal groove is exposed;

said metal body has an extended portion extending from a bottom surface of the groove and the extended portion has a remote end provided with a projection on a side thereof where the arch wire is placed, wherein the bottom surface is further recessed at a middle portion of the metal body in an arch wire extending direction.

11. A single type bracket adapted for being engaged with an arch wire, comprising:

a metal body having a groove to be engaged with the arch wire;

a synthetic resin housing securable to a tooth and accommodating the metal body therein such that a substantial area of an inner surface of the metal groove is exposed;

said metal body has an extended portion extending from a bottom surface of the groove and the extended portion has an end provided with a pair of projections on a side thereof where the arch wire is placed; and a recess adapted for a fastening wire to be engaged is provided on the extended portion on a side opposite to the side on which the arch wire is engaged.

12. An orthodontic bracket adapted for being engaged with an arch wire, comprising:

a metal body having a groove to be engaged with the arch wire;

a synthetic resin housing securable to a tooth and accommodating the metal body therein such that a substantial area of an inner surface of the metal groove is exposed;

said metal body has an extended portion extending from a bottom surface of the groove and the extended portion has a remote end provided with a projection on a side thereof where the arch wire is placed, wherein a recess, adapted for a fastening wire to secure the arch wire, is formed on the extended portion on a side opposite to the side on which the arch wire is placed.

13. The orthodontic bracket according to claim 12, wherein the recess is formed on the extended portion at a position corresponding to the projection in an arch wire extending direction.

* * * * *